United States Patent [19]

Untch et al.

[11] 4,123,550

[45] Oct. 31, 1978

[54] BICYCLO[3.1.0]HEXYLETHYLAMINOCARBONYL-SUBSTITUTED HETEROARYL CARDIOVASCULAR AGENTS

[75] Inventors: Karl G. Untch, Los Altos; Stefan H. Unger, Palo Alto; Brian Lewis, Mountain View, all of Calif.

[73] Assignee: Syntex (U.S.A.) Inc., Palo Alto, Calif.

[21] Appl. No.: 846,959

[22] Filed: Oct. 31, 1977

[51] Int. Cl.$^2$ .................. A01N 9/00; C07D 333/24
[52] U.S. Cl. .................. 424/275; 260/332.2 C; 260/307 FA; 424/272
[58] Field of Search .................. 260/332.2 C; 424/275

[56] References Cited

U.S. PATENT DOCUMENTS 3,897,441 7/1975 Edwards .................. 260/302 R

Primary Examiner—A. Siegel
Attorney, Agent, or Firm—Richard J. Hammond; Gerard A. Blaufarb

[57] ABSTRACT

1-Alkylamino-3-([2-(endobicyclo[3.1.0]hex-6-yl)ethylaminocarbonyl]thienyloxy)-2-propanols and methods for preparing these compounds are disclosed. The compounds are useful in the treatment of hypertension and abnormal heart conditions in mammals. These compounds are prepared by the treatment of the corresponding 1,2-epoxy-3-[2-(endobicyclo[3.1.0]hex-6-yl)ethylaminocarbonyl]heterocyclic aryloxy)propane with an alkylamine having the desired alkyl substituent or by base or acid hydrolysis of the corresponding 2-optionally substituted-3-alkyl-5-([2-(endobicyclo[3.1.0]hex-6-yl)ethylaminocarbonyl]heterocyclic aryloxymethyl)oxazolidine. These latter compounds can be prepared by condensing a halo-substituted thiophene with a 3-alkyl-5-hydroxymethyloxazolidine such substituted or unsubstituted at the 2-position or alternatively, by treating the former aminopropanol compounds of the present invention with an aldehyde having the desired substituent. These latter oxazolidine compounds are also active for treatment of hypertension and abnormal heart conditions.

15 Claims, No Drawings

BICYCLO[3.1.0]HEXYLETHYLAMINOCARBONYL-SUBSTITUTED HETEROARYL CARDIOVASCULAR AGENTS

FIELD OF INVENTION

The invention relates to 1-alkylamino-3-([2-(endobicyclo[3.1.0]hex-6-yl)ethylaminocarbonyl]thienyloxy)-2-propanol, and pharmaceutically acceptable salts thereof and to methods for preparing such compounds. This invention further relates to 2-optionally substituted-3-alkyl-5-[2(endobicyclo[3.1.0]hex-6-yl)ethylaminocarbonyl]thienyloxymethyl) oxazolidines, to pharmaceutically acceptable salts thereof and to methods for preparing such compounds. This invention also relates to pharmaceutical compositions comprising one or more of the above compounds and to methods for treating cardiac disorders and hypertension in mammals.

At the present time, the compound most frequently used in the United States for treatment of cardiac arrhythmias and hypertension is 1-(isopropylamino)-3-(1-naphthoxy)-2-propanol (e.g. Propranolol). Propanolol is believed to achieve its therpeutic action by competing with beta-adrenergic receptor stimulating agents for available beta receptor sites. When access to such sites is blocked by propranolol, the chronotropic, inotropic and vasodilator responses to beta-adrenergic stimulation is decreased. Such activity is however not specific. Not only are heart muscle receptor sites affected, but lung and related organs are found to be influenced by this drug. Contraindication is therefore indicated for patients with bronchial asthma, allergic rhinitis, sinus brachycardia and the like.

In order to overcome this disadvantage present in the non-specific beta-adrenergic blocking agents, drugs specific for heart muscle blockage only have been developed. See for example U.S. Pat. No. 3,408,387. One of the most active compounds of the selective beta blockers is N-[4(2-hydroxy-3-[(1-methylethyl)amino]-propoxy]acetanilide, e.g. practolol. Unfortunately, this compound exhibits disadvantageous side effects in man.

U.S. Pat. No. 3,897,441 discloses certain 3-(5-substituted aminocarbonylthiazol-2-yloxy)-2-propanol-1-amines and U.S. patent application Ser. No. 706,342 filed July 19, 1976 discloses various 5-carbocyclic alkylaminocarbonylthiazol-2-yloxy compounds. Both these compound-types display beta adrenergic blocking activity and cardiac selectivity. A block analogous class of compounds having surprising blocking activity, cardiac selectivity and reduced cardiac depression has now been discovered. These compounds are especially felicitous for the treatment or palliation of angina pectoris and cardiac arrhythmias and, because of their cardiac selectivity, can be safely applied to patients suffering from asthma or chronic obstructive lung disease.

SUMMARY

In summary, the compounds in accordance with the present invention can be represented by the following generic formula

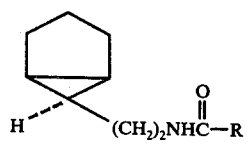

where R is

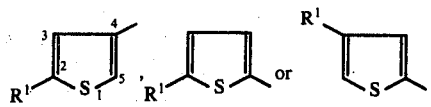

wherein $R^1$ is the radical

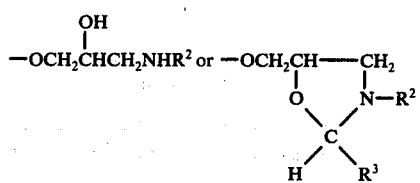

where $R_2$ is $C_1$ to $C_4$ linear or branched alkyl, $R^3$ is hydrogen, $C_1$ to $C_4$ linear or branched alkyl or $C_6$ to $C_{10}$ carbocyclic aryl optionally substituted with halo, $C_1$ to $C_4$ linear or branched alkyl, $C_1$ to $C_4$ linear or branched alkoxy, $C_2$ or $C_4$ linear or branched acyl, nitrile, nitro or $C_1$ to $C_4$ linear or branched carboalkoxy.

Also encompassed within the present invention are pharmaceutically acceptable salts of the above compounds.

The process of preparing the compounds of the present invention where $R^1$ is the radical

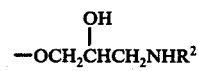

comprises treating the corresponding 1,2-epoxy-3-([2-(endobicyclo[3.1.0]hex-6-yl)ethylaminocarbonyl]thienyloxy) propane with an alkylamine having the desired alkyl substituent. Alternatively, the compounds can be prepared by the acid or base hydrolysis of the corresponding compounds of the present invention where $R^1$ is the radical

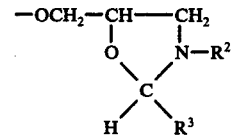

The process of preparing the compounds of the present invention where $R^1$ is the radical

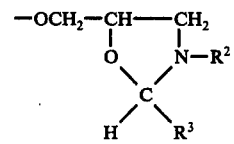

comprises condensing an [(endobicyclo[3.1.0]hex-6-yl)ethylaminocarbonyl]thienyloxy radical having the halo group at the desired position on the heteroaryl ring with a 5-hydroxymethyloxazolidine having the desired $R^2$ and $R^3$ substituents or treating the corresponding compounds of the invention where $R^1$ is the radical

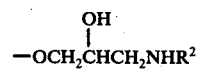

with the desired $R^3$ aldehyde.

The pharmaceutical compositions of the present invention include both solids or powders and solutions comprising one or more of the compounds of the invention in combination with a suitable pharmaceutical solvent, e.g. sterile water or pharmaceutical solid excipients.

The compounds in accordance with the present invention will be further discribed in the Description of the Preferred Embodiments.

DESCRIPTION OF THE PREFERRED EMBODIMENTS

The heterocyclic aryl compounds in accordance with the present invention are represented by the formula:

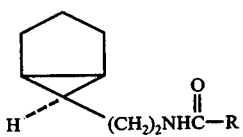

I where R is

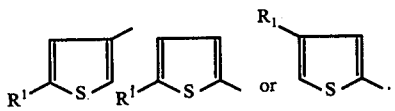

II

In the interest of brevity, the above heterocyclic aryl radicals will sometimes be referred to hereinafter as the radicals thienyl (II). The open bond on the above series (II) radicals represents the point of attachment to the group

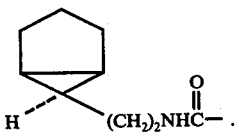

I

The group $R^1$ in the above series of radicals II is the group

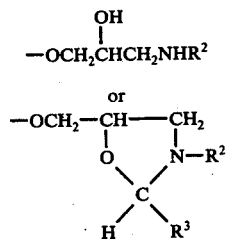

Ia or

Ib where $R^2$ is $C_1$ to $C_4$ linear or branched alkyl, and $R^3$ is hydrogen, $C_1$ to $C_4$ linear or branched alkyl or $C_6$ to $C_{10}$ carbocyclic aryl optionally substituted with halo, $C_1$ to $C_4$ linear or branched alkyl, $C_1$ to $C_4$ linear or branched alkoxy, $C_2$ to $C_4$ linear or branched acyl, nitrile, nitro, or $C_1$ to $C_4$ linear or branched carboalkoxy.

It should be understood that, the compounds of the present invention have asymmetric carbon atoms and can therefore exist as optically active isomers. Thus, the above formula is intended to represent the individual (+) or (−) optical isomers as well as the racemic mixtures thereof.

The pharmaceutically acceptable salts of the compounds of Formula I are also embraced by the present invention. By pharmaceutically acceptable salts is ment those pharmaceutically acceptable hydrogen organic or inorganic anion addition salts which do not adversely affect the pharmaceutical properties of the parent compound. Suitably organic anions include, for example acetate, benzoate, lactate, picrate, propionate, butyrate, valerate, tartrate, maleate, fumarate, citrate, succinate, tosylate, ascorbate, nicotinate, adipate, gluconate and the like. Suitable inorganic anions include for example chloride, bromide, iodide, sulfate, phosphate, nitrate and the like.

Typical illustrations of the compounds of the present invention and salts thereof can be had by references to the Examples. Where $R^1$ is

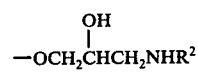

the preferred $R^2$ substituents are isopropyl or t-butyl, especially isopropyl.

The particularly preferred compounds in accordance with the present invention where $R^1$ is

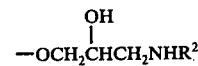

are:
1-isopropylamino-3-(5-[2-(endobicyclo[3.1.0]hex-6-yl)-ethylaminocarbonyl]thien-2-yloxy)-2-propanol;
1-t-butylamino-3-(5-[2-(endobicyclo[3.1.0]hex-6-yl)-ethylaminocarbonyl]thien-2-yloxy)-2-propanol;
1-isopropylamino-3-(5-[2-(endobicyclo[3.1.0]hex-6-yl)-ethylaminocarbonyl]thien-3-yloxy)-2-propanol;
1-t-butylamino-3-(5-[2-(endobicyclo[3.1.0]hex-6-yl)-ethylaminocarbonyl]thien-3-yloxy)-2-propanol;
1-isopropylamino-3-(4-[2-(endobicyclo[3.1.0]hex-6-yl)-ethylaminocarbonyl]thien-2-yloxy)-2-propanol;
1-t-butylamino-3-(4-[2-(endobicyclo[3.1.0]hex-6-yl)-ethylaminocarbonyl]thien-2-yloxy)-2-propanol.

The preferred compounds of the present invention where $R^1$ is

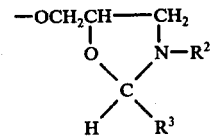

are $R^2$ being isopropyl or t-butyl. In the case of $R^3$ the aromatic substituents are preferred, such being $C_6$ to $C_{10}$ carbocyclic aryl preferably phenyl optionally substituted with preferably halo, methyl, methoxy, acetoxy, nitrile or nitro.

The particularly preferred compounds in accordance with the present invention where $R^1$ is

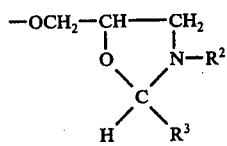

are:

2-phenyl-3-isopropyl-5-(5-[2-(endobicyclo[3.1.0]hex-6-yl)ethylaminocarbonyl]thien-2-yloxymethyl)oxazolidine, 2-phenyl-3-t-butyl-5-(5-[2-(endobicyclo[3.1.0]hex-6-yl)ethylaminocarbonyl]thien-2-yloxymethyl)oxazolidine and the like.

The preferred pharmaceutically acceptable salts are the hydrogen addition salts of the bromide, sulfate, lactate, tartrate, succinate, and especially chloride and maleate. The preferred salts are the preferred anion addition salts of the compounds in accordance with the present invention and correspondingly the particularly preferred salts are the preferred hydrogen-anion addition salts of the preferred and particularly preferred compounds herein, and especially the hydrochloride and maleate salts.

The compounds in accordance with the present invention are conveniently prepared by applying many of the procedures disclosed in the before referenced U.S. Pat. application Ser. No. 706,412 filed July 19, 1976. Particularly, the compounds of the present invention where $R^1$ is

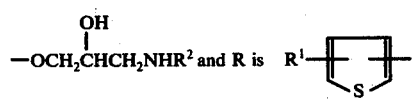

—OCH$_2$CHCH$_2$NHR$^2$ and R is wherein $R^1$ is at the positions 2 or 3 and the open bond, i.e., the point of attachment to the group 2-(endobicyclo[3.1.0]hex-6-yl)ethylaminocarbonyl is at positions 4 or 5, are readily prepared from the corresponding thienyloxypropane acetonide substituted at the desired ring position with the 2-endobicyclo[3.1.0]hex-6-yl)ethylaminocarbonyl group. Illustrative of the reaction path for obtaining the thienyl compounds of the present invention from the aforesaid acetonide are the reactions set forth below where the preparation of 1-isopropylamino-3-(5-[2-(endobicyclo[3.1.0]hex-6-yl)ethylaminocarbonyl]thien-2-yloxy-2-propanol is illustrated.

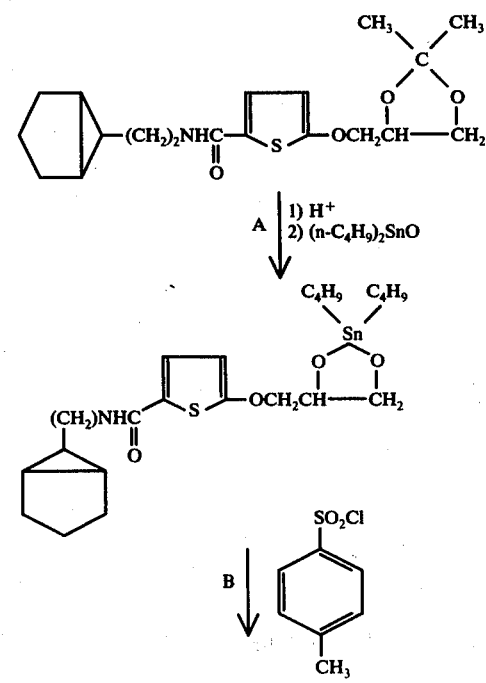

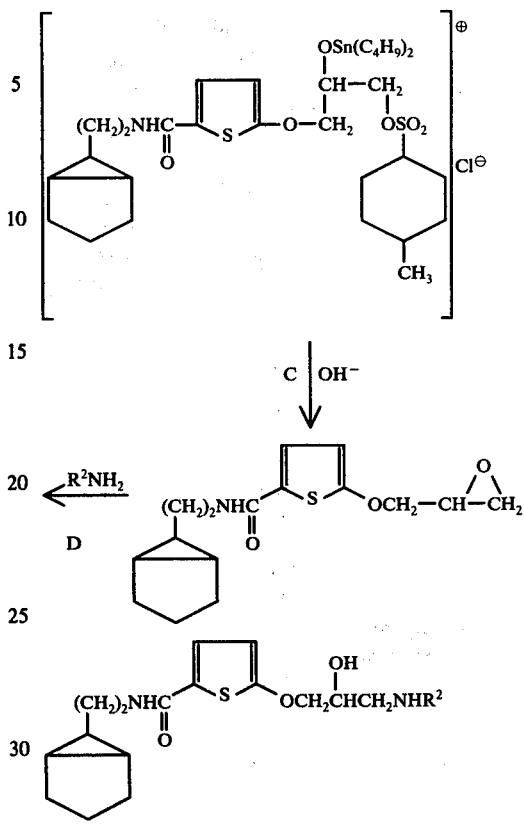

Reaction sequence A, a two step reaction, utilizes a strong acid (step 1) to effect the ring opening of the acetonide starting material. Any of the common strong organic acids can be used such illustrated by trifluoro- or trichloroacetic acid, and the like or the strong inorganic acids such as sulfuric acid, hydrochloric acid and the like. The reaction is typically carried out in an inert polar solvent such as methanol, water or mixtures thereof at room temperature to about 100° C. for times sufficient to achieve the ring opening to the vicinal diol intermediate (not shown), preferably about thirty minutes. The step 2 reaction to yield the stannadioxalane is typically carried out at 50° to 100° C., preferably 50° to 75° C. from about 30 minutes to about 6 hours, preferably 1 to 2 hours. The stannadioxalane product need not be isolated as such but can be used directly without purification in the next step of the reaction, i.e., reaction sequence B. In this reaction sequence, the stannadioxalane ring is broken to yield a stannous salt-like intermediate. Such ring opening is achieved with any material that will break the stannadioxalane ring and at the same time attach itself at the 3 position of the propoxy chain in the form of a leaving group. While tosylchloride is shown in the illustrative scheme B, any of the well known leaving group-type reagents can be used herein. As such, mesylchloride can be used to achieve the ring opening of the stannadioxalane compounds with subsequent substitution on the propyl side chain. The reaction sequence B is preferably carried out in an inert organic solvent such as methylene chloride, dichloroethane and the like, typically at temperatures of from 20° to 100° C., preferably 35° to 75° C. for about five to about sixty, preferably fifteen, minutes. As in the case of sequence A, the product of the ring opening reaction need not be directly isolated but can be used without isolation for the subsequent reaction sequence C. Reaction sequence C is a base catalyzed ring closure of the type well known in the prior art. To effect such, it is conventional to use a strong base such as an alkali or alkaline earth metal hydroxide, carbonate or alkoxide. Typically the strong base is added to the reaction solution of reaction sequence B at −30° to +25° C., preferably 0° C. for about 5 to about 60 minutes. The resulting compound i.e. the epoxide, is preferably isolated before being used as the starting material for the final step of the reaction. Such isolation can be effected by conventional separation procedures such as, for example, precipitation with water, extraction, crystallization or chromatography. Specific illustrations of typical separation and isolation procedures can be had by reference to the appropriate Preparations herein below.

The compounds of the present invention where $R^1$ is

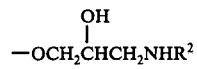

can be conveniently prepared by treating the epoxide formed above with a monoalkylamine having the desired alkyl substituent. Typically, this treatment is conducted in an inert organic solvent and is typically conducted at temperatures in the range of from about −10° to about 100° C., preferably about 20° to about 60° C. for about from one hour to forty-eight hours, preferably about three to eighteen hours. Typically, the ratio of alkylamine: epoxide in sequence D is in the range of from about 1 to 30:1 preferably from about 1 to 10:1. Suitable alkylamines which can be used include for example, methylamine, ethylamine, isopropylamine, t-butylamine, and the like. Suitable inert organic solvents which can be used include for example methanol, ethanol, monoglyme and the like and mixtures thereof. The resulting products can then be separated and isolated according to conventional procedures, such as, for example evaporation, crystallization, chromotography, etc. Specific illustrations of typical separation and isolation procedures can be had by reference to the corresponding Examples, set forth hereinbelow.

The compounds of the present invention where $R^1$ is

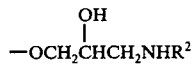

prepared as illustrated in the above reaction series are used to prepare directly the corresponding compounds of the present invention where $R^1$ is

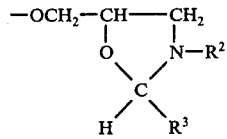

wherein $R^2$ and $R^3$ are defined hereinabove.

The reaction to form the above compounds having the substituent Ib can be conveniently effected by treating the corresponding compound where $R^1$ is

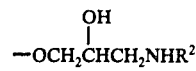

with an aldehyde having the desired $R^3$ substituent. This reaction can be effected by simply treating the compound of reaction sequence D with the desired aldehyde using a lower alcohol (e.g. ethanol) as solvent. Typically a mole ratio of from about 1 to about 10 moles of aldehyde is used per mole of compound where $R^1$ is

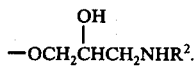

The reaction is typically conducted at temperatures in the range of from about 20° to about 100° C. for about from one to about forty-eight hours. Suitable aldehydes which can be used in this reaction include for example p-acetylbenzaldehyde, p-cyanobenzaldehyde, p-chlorobenzaldehyde, acetaldehyde, formaldehyde and the like. Alternatively, the oxazolidine compounds in accordance with the present invention bearing the substituent Ib can be prepared by the following reaction:

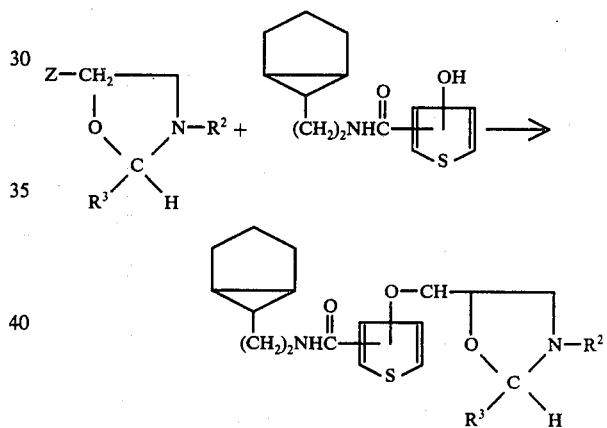

where the endobicyclo[3.1.0]hexyl-containing substituent is at positions 2 or 3 and the OH radical at positions 4 or 5, Z is any readily displaceable group such as halo, mesyloxy, tosyloxy and the like and $R^2$ and $R^3$ are described above.

This reaction is conveniently carried out by first treating the 5-hydroxymethyl-3-alkyl-2-optionally substituted oxazolidine with a reagent that will react with the hydroxy moiety of the 5-hydroxymethyl group thereby forming an intermediate bearing a 5-methyl-leaving group-substituted oxazolidine (the group Z). Such displaceable leaving groups are well known in the prior art, e.g., the reactions of alcohols with selected reagents to yield leaving group-substituted intermediates. See for example Fieser & Fieser, Reagents for Organic Synthesis, page 662 (1967) and the Examples therein. Preferably the leaving group Z is tosyloxy or mesyloxy. After isolation of the Z-substituted oxazolidine, the displacement is affected by subsequent reaction with the desired substituted thiophenoxy anion to yield the oxazolidine bearing the group I$b$. Typically, the leaving group-substituted oxazolidine is formed by reaction of methanesulfonylchloride or p-toluenesulfonylchloride with the oxazolidine alcohol in the presence of an acid acceptor-containing solution. Typical acid acceptors are the trialkyl- or arylamines or alkali metal carbonates. The subsequent reaction with the thiophene alcohol is accomplished by first activating the alcohol typically with an alkali metal hydride such at temperatures of about −10° to about 100° C. preferably 0° to 30° C. for about one minute to about 1 hour preferably five minutes to 20 minutes. The oxazolidine dissolved in a suitable inert organic solvent is next added and the mixture allowed to react to form about 25° to about 100° C. preferably 70° to 90° C. for about 1 hour to about 8 hours preferably 1 hour to 3 hours. Typically the ratio of 5-hydroxymethyl-substituted oxazolidine:leaving group reagent is in the range 1 to 5:1, preferably 1 to 1.5:1. The ratio of 5-leaving group-substituted oxazolidine:thiophene alcohol:alkali metal hydride is in the range 1 to 5:1:1 to 2, preferably 1.3:1:1.1.

The oxazolidine product can then be separated and purified according to conventional procedures such as, for example, illustrated in the Examples hereinbelow. Care should be exercised during the purification procedure as compounds I of the present invention bearing the oxazolidine substituent are readily hydrolyzed to the compounds of the present invention where $R^1$ equals

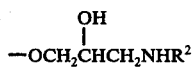

by both acid and basic conditions. Correspondingly, the compounds of the present invention where $R^1$ is

can be prepared by the simple acid or base hydrolysis of the corresponding compounds of the present invention bearing the substituent Ib. Acid hydrolysis can be conveniently effected by treating the oxazolidine compound with suitable organic acids such as, for example, acetic acid, formic acid, oxalic acid and the like or suitable inorganic acids such as, for example, hydrochloric acid, sulfuric acid and the like. Preferably the hydrolysis is conducted under mildly acidic conditions. Similarly basic hydrolysis can be conducted by treating the oxazolidine compound with a suitable base such as, for example, dilute sodium hydroxide, potassium hydroxide and the like. Preferably this hydrolysis is conducted under mildly alkaline conditions. Alternatively, the hydrolysis can be conducted by exchange with a suitable ion exchange resin in either the H+ or OH− form.

The bicyclic acetonide shown as the starting material in the reaction sequence A through D is readily prepared by the reaction sequence shown below.

Conveniently the following reaction scheme has been utilized herein:

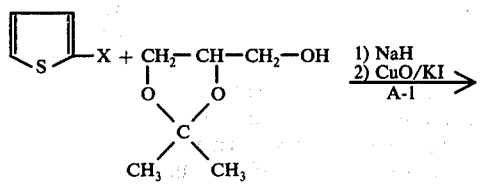

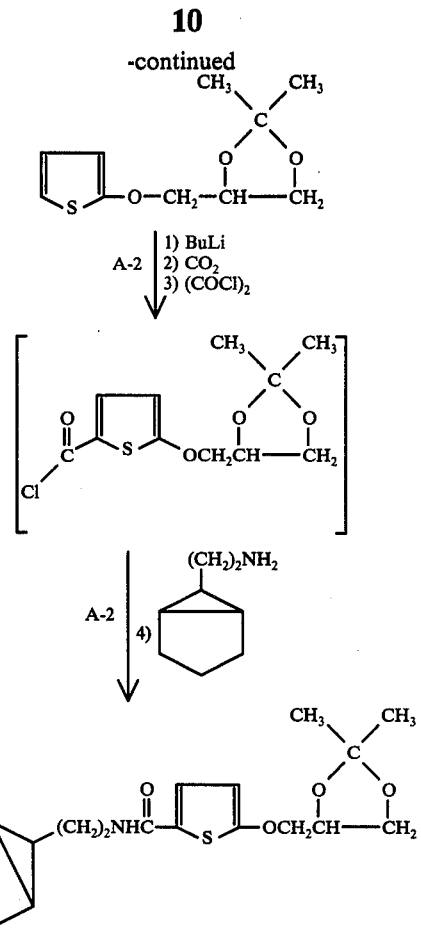

wherein X is halo such as bromo or chloro.

The readily available halothiophene, such as illustrated by the 2-bromothiophene is first converted to its acetonide. An alkali metal hydride is first reacted with solketal (A-1, step 1). The reaction is run at low temperatures, e.g., from −25° to +25° C. preferably around 5° C. using excess solketal as solvent medium. The bromothiophene, cupric oxide and potassium iodide are then added, (A-1, Step 2). Typically, this reaction is conducted at temperatures of from about 100° to 200° C. for from about 15 to 48 hours. The product of the reaction sequence A-1, a 1,2-dihydroxy-3-thienyloxy propane acetonide is then separated from the reaction solution by any conventional separation means and used as the starting material for reaction A-2. The carbonylation reaction A-2 of aromatic anions is well known in the prior art and has been described in detail in a variety of references, i.e., see for example Organic Synthesis, Coll. Vol. I, 361 (1941)., ibid. page 542 and ibid Vol. 2, 425 (1943). Typically, the acetonide of Sequence A-1 is dissolved in an appropriate anhydrous organic solvent, such as tetrahydrofuran, and an alkyl lithium is added, typically keeping the temperature of the reaction to about from −100° to −50° C. (A-2, Step 1). Dry carbon dioxide gas is then passed into the solution, precipitating out the carboxylic acid lithium salt (A-2, Step 2).

In A-2, Step 3, the addition of an appropriate acid halide, such as oxalyl chloride, typically at about −100° to about 75° C., preferably −80° to −30° C., forms the thiophene acid halide. After driving off the residual $CO_2$ and CO absorbed in the solution (for example by heating the reaction solution to reflux temperature), reaction sequence A-3, Step 3 can be readily carried out without further isolation of the intermediate. Subsequent reaction (A-2, Step 4) reacts the acid chloride of A-2, Step 3 with 2-(endobicyclo[3.1.0]hex-6-yl)ethylamine in the presence of a suitable acid acceptor at −30° to 50° C. yielding the precursor compound shown as the starting material in the reaction series A hereinabove. While steps 1 through 4 of sequence A-2 are preferably conducted in a single reaction vessel without isolation of the intermediates, the A-2 reaction sequence can be stopped at any convenient place in the process and a given intermediate isolated.

The pharmaceutically acceptable acid addition salts of the compounds of the present invention can be prepared from the parent compounds via careful neutralization with the desired acid. Other pharmaceutically acceptable addition salts can then be conveniently prepared from the addition salts via anion exchange with a suitable ion exchange resin in the desired anionic form.

The compounds of the invention are useful in the treatment and palliation of cardiovascular abnormalities in mammals. These compounds primarily achieve their therapeutic action by selectively blocking the cardiac beta-adrenergic receptor sites and, accordingly, because they are cardiac selective, they can also be applied to treat cardiac abnormalities in patients suffering from asthma or chronic obstructive lung disease.

The compounds are especially useful in the treatment or palliation of cardiac arrhythmias, angina pectoris, hypertrophic subaortic stenosis, pheochromocytoma, thyrotoxicosis, hyperkenetic syndromes, tetrology of Fallot, mitral stenosis with tachycardia, general ischemic conditions, and hypertension founded on elevated cardiac outputs due to a hyperadrenergic state. The compounds are active, both in the treatment or palliation of acute attacks of such cardiac disorders, and further can be applied prophylactically to prevent or reduce the frequency of such attacks. This prophylactic action is particularly desirable in reducing the frequency of attacks of angina pectoris, since the medication (i.e. nitroglycerin) presently commonly used in the treatment of angina pectoris has no recognized prophylactic action. Additional information concerning the use, action and determination of beta-blockers can be obtained by reference to the literature such as, for example, Dotlery et al, *Clinical Pharmacology and Therapeutics*, Volume 10, No. 6, 765–797 and the references cited therein.

The compounds of the invention are also useful in the treatment of hypertension in mammals.

The compounds of this invention are typically administered, both for the treatment of cardiac disorders and hypertension, in dosages of from about 0.01 to 5 mg per kg. of body weight. The precise effective dosage will, of course, vary depending upon the mode of administration, the condition being treated and the host. Where the compounds are used to treat cardiac conditions such as arrhythmias, the compounds are typically administered either orally or intravenously. Where the compounds are administered to treat hypertension or cardiac conditions such as angina pectoris, the compounds are, for the sake of convenience, typically administered orally.

The compounds of the invention can be administered for the treatment of cardiac disorders and hypertension in a wide variety of dosage forms, either alone or in combination with other pharmaceutically compatible medicaments, in the form of pharmaceutical compositions suited for oral or parenteral administration. The compounds are typically administered as pharmaceutical compositions consisting essentially of the compounds of the invention and a pharmaceutical carrier. The compounds are typically administered as pharmaceutically acceptable salts. The pharmaceutical carrier can be either a solid material or liquid, in which the compound is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups or elixirs and optionally can contain small quantities of preservatives and/or buffering agents, and preferably contain the therapeutic agent in convenient unit dosage concentrations.

The solid compositions can take the form of tablets, powders, capsules, pills or the like, preferably in unit dosage forms for simple administration or precise dosages. Suitable solid carriers include, for example, pharmaceutical grades of starch, lactose, sodium saccharine, sodium bisulfite and the like.

Also based on studies on related compounds, it can be predicted that a number of the present compounds will exhibit useful local anesthetic activity. Where the compounds are applied as local anesthetics, they can be administered topically, intradermally or subcutaneously.

A further understanding of the invention can be had from the following non-limiting Preparations and Examples. Also as used hereinabove and below unless expressly stated to the contrary, all temperatures and temperature ranges refer to the Centrigrade system and the terms ambient or room temperature refer to about 20° C. The term percent or (%) refers to weight percent and the term mole or moles refers to gram moles. The term equivalent refers to a quantity of reagent equal in moles to the moles of the preceding or succeeding reactant recited in that Preparation or Example in terms of moles or finite weight or volume.

Proton or $^{13}$carbon nuclear magnetic resonance spectra $^1$H NMR and $^{13}$C NMR are determined at 60, 90 and MHz (the signs of the coupling constants are not assigned) and signals are assigned as singlets(s), broad singlets(bs), doublets(d), broad doublets(dd), triplets(t), double triplets(dt), quartets(g) and multiplets(m) and recorded in S from tetramethylsilane as internal standard. Compounds having assemetric centers and optical activity are isolated in their (±) racemic form, unless otherwise indicated.

Preparation 1

2-(Endobicyclo[3.1.0]hex-6-yl)ethylamine a. In this preparation 1.9 g. (0.05 mole) of lithium aluminum hydride is dissolved in 100 ml. of diethyl ether, under nitrogen, cooled to C° C., and then 10.8 g. (0.1 mole) of endobicyclo[3.1.0]hex-2-en-6-yl carboxaldehyde in 100 ml. of diethyl ether is added dropwise. The mixture is allowed to warm to room temperature, and then stirred for 30 minutes. Ten milliliters of ethyl acetate is added, and then 10 ml. of water. The mixture is filtered and the filtrate dried with anhydrous magnesium sulfate, filtered, and the filtrate evaporated under vacuum affording 6-(hydroxymethyl)endobicyclo[3.1.0]hex-2-ene.

b. A mixture containing 10 g. (0.091 mole) of 6-(hydroxymethyl)-endobicyclo[3.1.0]hex-2-ene and 0.5 g. of 5% platinum on carbon in 250 ml. of ethyl acetate is stirred under hydrogen, at room temperature, until no further hydrogen is absorbed (about two liters is absorbed). The catalyst is removed by filtration and the filtrate evaporated under vacuum affording 6-(hydroxymethyl)-endobicyclo[3.1.0]hexane.

c. Ten grams (0.089 mole) of 6-(hydroxymethyl)-endobicyclo[3.1.0]hexane is mixed with 23.4 g. (0.089 mole) of triphenylphosphine in 40 ml. of carbon tetrachloride and heated, under nitrogen, at 60° C. for 4 hours. The mixture is poured into 200 ml. of hexane, stirred, and then filtered, the filtrate concentrated by evaporation under vacuum. The concentrate is then chromatographed on silica gel, eluting with 5% ethyl acetate-95% (vol.) hexane, affording 6-(chloromethyl)-endobicyclo[3.1.0]hexane.

d. A mixture containing 9 g. (0.069 mole) of 6-(chloroethyl)-endobicyclo[3.1.0]hexane and 4.9 g. (0.1 mole) of sodium cyanide in 100 ml. of dimethylsulfoxide is heated at 70° C., under nitrogen, for 4 hours, and then poured into 500 ml. of methylene chloride. The mixture is washed three times with water, dried over anhydrous magnesium sulfate, and filtered. The filtrate is evaporated under vacuum and the resulting residue chromatographed on silica gel, eluting with 5% ethyl acetate-95% (vol.) hexane affording endobicyclo[3.1.0]hex-6-yl acetonitrile.

e. 2.2 Grams (0.058 mole) of lithium aluminum hydride is dissolved in 100 ml. of anhydrous diethyl ether at 0° C., under nitrogen, and 7 g. (0.058 mole) of endobicyclo[3.1.0]hex-6-yl acetonitrile in 100 ml. of diethyl ether is added dropwise. The mixture is maintained at 0° C. for 30 minutes and 10 ml. of water carefully added. The resulting mixture is filtered, the filtrate is dried over potassium hydroxide pellets, filtered again, and the filtrate distilled to remove the ethyl ether solvent, affording 2-(endobicyclo[3.1.0]-hex-6-yl)ethylamine.

Preparation 2

2-[2-(endobicyclo[3.1.0]hex-6-yl)ethylaminocarbonyl]-4-bromothiophene

In a reaction flask 28.5 g. of freshly distilled thionyl chloride is admixed with 34.2 g. of 4-bromothiophene-2-carboxylic acid. The mixture is stirred and heated slowly. When the temperature of the reaction reaches 70° C. copious evolution of sulfur dioxide and hydrogen chloride occurs. The temperature is maintained at 68°–70° C. for an additional 1½ hours. Residual thionyl chloride is evaporated (vacuum) and the reaction mass cooled to room temperature. The residue is dissolved in 150 ml. dry toluene. To this solution is added a solution of 24.9 g. 2-(endobicyclo[3.1.0]hex-6-yl)ethylamine in 150 ml. dry toluene together with an equivalent amount of triethylamine, with cooling to about 0° C., 30 minute addition time. After the addition the reaction solution is allowed to warm to room temperature with continued stirring for an additional 1½ hours. The solution is washed with water (3 times, 150 ml. each) and dried over anhydrous magnesium sulfate. Removal of the solvent (vacuum) affords the captioned compound.

Similarly prepared, using 2-bromothiophene-4-carboxylic acid, is 4-[2-(endobicyclo[3.1.0]hex-6-yl)ethylaminocarbonyl]-2-bromothiophene.

Preparation 3

Thiophene-Substituted 1,2-Dihydroxypropanol Acetonide Preparations a. To 350 ml. of solketal, 25 g. of sodium hydride are added at 5° C. After the completion of reaction, 100 g. of 2-bromothiophene, 20 g. of cupric oxide and 500 mg. of potassium iodide are added and the mixture heated at 160° for 44 hours. After cooling to room temperature, 200 ml. of water is slowly added to the reaction. The resulting aqueous mixture is extracted with hexane (3 times, 100 ml. each) and the hexane solution washed with water, dried over magnesium sulfate and evaporated to dryness (vacuum). Distillation of the oily residue gives 1,2-dihydroxy-3-(thien-2-yloxy)propane acetonide, 100 g. b.p. 96°–97° (1 mm).

b. In a similar manner, substituting for the 2-bromothiophene the compounds illustrated in Preparation 2, the following are prepared:

1,2-dihydroxy-3-(2-[2-(bicyclo[3.1.0]hex-6-yl)ethylaminocarbonyl]thien-4-yloxy)propane acetonide;

1,2-dihydroxy-3-(4-[2-(bicyclo[3.1.0]hex-6-yl)ethylaminocarbonyl]thien-2-yloxy)propane acetonide.

Preparation 4

1,2-dihydroxy-3-(5-[2-(endobicyclo[3.1.0]hex-6-yl)ethylaminocarbonyl]thien-2-yloxy)propane acetonide To 6.62 g. of the acetonide of Preparation 3 in 150 ml. tetrahydrofuran, at −78°, is added 21 ml. of n-butyl lithium. The mixture, under nitrogen, is kept at −78° for 55 min. Dry carbon dioxide gas is then passed through the solution, causing 1,2-dihydroxy-3-(3-carboxythien-2-yloxy)propane acetonide, lithium salt to precipitate. At −78°, 4.0 g. of oxalyl chloride are added and the reaction mixture is gradually heated to reflux. After the evolution of $CO_2$ + CO ceases (the acid chloride is formed at this point—see reaction sequence A-2, step 3) the solution is cooled to 0°, and a mixture of 4.0 g. of triethylamine and 4.0 g. of 2-(endobicyclo[3.1.0-]hex-6-yl)ethylamine is added. The solution is heated for 15 minutes to complete the reaction. After the evaporation of tetrahydrofuran, the residue is dissolved in methylene chloride (150 ml.), washed with water, 10% aqueous acetic acid, 10% sodium bicarbonate, dried over magnesium sulfate and evaporated to dryness (vacuum) to give 10 g. of the captioned product, isolated as an oil. $^1$HNMR in $CDCl_3$ 0.4–2.0 (m, 11H; CH and $CH_2$)
1.40 (s, 3H; acetonide methyls)
1.45 (s, 3H; acetonide methyls)
3.48 (q, 2H, J=6.5 Hz; $NCH_2$)
3.7–4.6 (m, 5H; $OCH_2$, $OCH_2$ OCH)
6.23 (d, 1H, J=4.0 Hz; H3)
7.21 (d, 1H, J=4.0 Hz; H4)

Preparation 5

1,2-epoxy-3-(5-[2-(endobicyclo[3.1.0]hex-6-yl)ethylaminocarbonyl]thien-2-yloxy)propane To a solution of 10 g. of the compound illustrated in Preparation 4 in 150 ml. of methanol, 20 ml. of water and 1.5 ml. of trifluoroacetic acid is added and the solution refluxed for 30 minutes. Thereafter all solvents are removed under reduced pressure affording 3-(5-[2-(endobicyclo[3.1.0]hex-6-yl)ethylaminocarbonyl]thien-2-yloxy)propane-1,2-diol. The diol and 10.5 g. of dibutyl tin oxide are treated with 200 ml. of methanol. The mixture is heated to reflux for 1 hour affording 4-(5-[2-(endobicyclo[3.1.0]hex-6-yl)ethylaminocarbonyl]thien-2-yloxy)methyl-2-stanna-1,3-dioxalane. The majority of methanol is removed under vacuum and final traces are removed azeotropically with toluene. To the above stannadioxalane a solution of 200 ml. methylene chloride and 8.5 g. of p-toluene solfonyl chloride is added. The mixture is refluxed for 15 minutes and the solution cooled at 0°. 10 Grams of potassium hydroxide in 10 ml. of water is next added to the mixture and stirred for 30 minutes. The mixture is filtered through a Celite and charcoal bed, and the bed washed with 50 ml. (2 times) methylene chloride. The resulting solution is washed with water dried over magnesium sulfate and evaporated to dryness (vacuum). The captioned compound is isolated via preparative TLC plates, 1.5 g. crystalline solid.

$^1$H NMR in $CDCl_3$
0.6–2.0 (m; 11H; CH and $CH_2$)
2.75 (m, 2H; $O-CH_2$)
3.3 (m, 1H; OCH)
3.45 (q, 2H, J=6.5; $N-CH_2$)
3.90 (dd, 1H, J=11.0, 6.0 Hz; $Ar-OCH_2$)
4.28 (dd, 1H, J=11.0, 3.0 Hz; $ArOCH_2$)
6.20 (d, 1H, J=4Hz; Aromatic-H)
7.17 (d, 1H, J=4Hz; Aromatic H)

Using the same procedure, but substituting for the above acetonide
1,2-dihydroxy-3-(2-[2-(endobicyclo[3.1.0]hex-6-yl)ethylaminocarbonyl]thien-4-yloxy)propane acetonide and
1,2-dihydroxy-3-(4-[2-(endobicyclo[3.1.0]hex-6-yl)ethylaminocarbonyl]thien-2-yloxy)propane acetonide, the following are prepared:
1,2-epoxy-3-(2-[2-(endobicyclo[3.1.0]hex-6-yl)ethylaminocarbonyl]thien-4-yloxy)propane;
1,2-epoxy-3-(4-[2-(endobicyclo[3.1.0]hex-6-yl)ethylaminocarbonyl]thien-2-yloxy)propane.

EXAMPLE 1

1-Isopropylamino-3-(5-[2-(endobicyclo[3.1.0]hex-6-yl)ethylaminocarbonyl]thien-2-yloxy)-2-propanol.

To 900 mg. of the compound illustrated in Preparation 5 in 20 ml. methanol is added 5 ml. of isopropylamine, and the mixture is stirred at room temperature for 16 hours. The above captioned compound, after removal of methanol and excess amine, is isolated via preparative TLC plates, 290 mg. m.p. 75°–77° (methanol-ether).

Using the same procedure as above but substituting the other epoxides illustrated in Preparation 5 the following are prepared:
1-isopropylamino-3-(2-[2-(endobicyclo[3.1.0]hex-6-yl)ethylaminocarbonyl]thien-4-yloxy)-2-propanol;
1-isopropylamino-3-(4-[2-(endobicyclo[3.1.0]hex-6-yl)ethylaminocarbonyl]thien-4-yloxy)-2-propanol.

Using the same procedure as above, but substituting t-butylamine for isopropylamine, the following are prepared:
1-t-butylamino-3-(5-[2-(endobicyclo[3.1.0]hex-6-yl)ethylaminocarbonyl]thien-2-yloxy)-2-propanol;
1-t-butylamino-3-(2-[2-(endobicyclo[3.1.0]hex-6-yl)ethylaminocarbonyl]thien-4-yloxy)-2-propanol;
1-t-butylamino-3-(4-[2-(endobicyclo[3.1.0]hex-6-yl)ethylaminocarbonyl]thien-2-yloxy)-2-propanol.

EXAMPLE 2

This example illustrates methods of preparing hydrochloride addition salts of the compounds of the present invention having the substituent of formula Ia. In this Example 1 g. of 1-isopropylamino-3-(5-[2-(endobicyclo[3.1.0]hex-6-yl)ethylaminocarbonyl]thien-2-yloxy)-2-propanol is dissolved in 10 ml. of ethyl ether at 20° C. A stream of gaseous anhydrous hydrogen chloride is passed over the surface of the solution until the supernatent liquid becomes colorless. The resulting precipitate is collected by filtration, washed with ethyl ether and then crystallized from methanol/diethyl ether, affording crystalline 1-isopropylamino-3-(5-[2-(endobicyclo[3.1.0]hex-6-yl)ethylaminocarbonyl]thien-2-yloxy)-2-propanol hydrochloride.

Similarly, by following the same procedure, the corresponding hydrochloride addition salts of each of the products of Example 1 are respectively prepared.

EXAMPLE 3

This example illustrates methods of preparing the maleate addition salts of the compounds of the present invention having the substituent of formula Ia. In this Example 1 g. of i-isopropylamino-3-(5-[2-(endobicyclo[3.1.0]hex-6-yl)ethylaminocarbonyl]thien-2-yloxy)-2-propanol is dissolved in a solution of 5 ml. of ethyl ether and 5 ml. of ethanol at 20° C. To this solution is added 10 ml. of a saturated solution of maleic acid in ethyl ether. The mixture is allowed to stand for one hour at room temperature. The resulting precipitate is recovered by filtration, washed three time with ethyl ether and then crystallized from a mixture of ethyl ether and ethanol affording crystalline 1-isopropylamino-3-(5-[2-(endobicyclo[3.1.0]hex-6-yl)ethylaminocarbonyl]thien-2-yloxy)-2-propanol maleate.

Similarly, by following the same procedure, the corresponding maleate salts of each of the products of Example 1 are prepared.

EXAMPLE 4

This Example illustrates the method of converting the compounds where $R^1$ is the substituent Ia into the corresponding compounds where $R^1$ is the substituent Ib. In this Example, 1 mmole of 1-isopropylamino-3-(5-[2-(endobicyclo[3.1.0]hex-6-yl)ethylaminocarbonyl]thien-2-yloxy)-2-propanol in 10 ml. of methanol is admixed with 20 ml. of acetaldehyde and 2 g. aluminum isopropoxide and then stirred at room temperature for one hour. The solvent is then removed by evaporation under vacuum affording 2-methyl-3-isopropyl-5-(5-[2-(endobicyclo[3.1.0]hex-6-yl)ethylaminocarbonyl]thien-2-yloxymethyl)oxazolidine.

Similarly by following the same procedure but using other aldehydes in place of acetaldehyde, the corresponding 2-substituted 3-isopropyl-oxazolidine analogs of the above products are respectively prepared. By replacing the above compound where $R^1$ is the substituent Ia with other compounds of the present invention where $R^1$ is substituent Ia, other 2-substituted oxazolidine compounds can be prepared with various 2 and 3 substitutions on the oxazolidine ring.

EXAMPLE 5

This Example illustrates the method of converting the compounds bearing the group Ib into the compounds bearing the group Ia of the invention. In this Example, 1 g. of 2-phenyl-3-t-butyl-5-(5-[2-(endobicyclo[3.1.0]hex-6-yl)ethylaminocarbonyl]thien-2-yloxymethyl)oxazolidine is dissolved in 50 ml. of ethyl acetate and this solution is treated with aqueous 5% sodium hydroxide (20 ml.) at 20° C. The mixture is allowed to stand with intermitant shaking for 0.5 hours, washed three times with water, dried over magnesium sulfate and then evaporated to dryness, affording 1-t-butylamino-3-(5-[2-(endobicyclo[3.1.0]hex-6-yl)ethylaminocarbonyl]thien-2-yloxy)-2-propanol.

Similarly, by following the same procedures, the products of Example 4 are respectively hydrolyzed to the corresponding compounds having the substituent Ia.

EXAMPLE 6

This example illustrates an alternate method for converting the compounds having the substituent Ib to the compounds having the substituent Ia. In this example 1 g. of 2-phenyl-3-t-butyl-5-(5-[2-(endobicyclo[3.1.0]hex-6-yl)ethylaminocarbonyl]thien-2-yloxymethyl)oxazolidine is dissolved in 20 ml. of methanol containing 4 ml. of 5% aqueous hydrochloric acid at 20° C. After 15 minutes, the mixture is neutralized with dilute aqueous sodium carbonate solution, poured into water and extracted with ethyl acetate. The ethyl acetate extract is evaporated to dryness yielding 1-t-butylamino-3-(5-[2-(endobicyclo[3.1.0]hex-6-yl)ethylaminocarbonyl]thien-2-yloxy)-2-propanol.

Similarly, by following the same procedure, the products of Example 4 are respectively hydrolyzed to the corresponding compounds of substituent Ia.

EXAMPLE 7

This Example illustrates an alternate method for the preparation of the compounds of the present invention having the substituent Ib.
2-Phenyl-3-t-butyl-5-(4-[2-(endobicyclo[3.1.0]hex-6-yl)ethylaminocarbonyl]thien-2-yloxymethyl)oxazolidine.

(a) 2-phenyl-3-t-butyl-5-p-toluenesulfonyloxymethyloxazolidine

To a solution of 2-phenyl-3-t-butyl-5-hydroxymethyloxazolidine (12.05 g.) in triethylamine (120 ml.) is added p-toluenesulfonylchloride (14.5 g.). After 6 days at room temperature the mixture is added to water (500 ml.) and extracted with ether (2 × 200 ml.). The ether solution is washed with water, dried with anhydrous magnesium sulfate and evaporated to dryness. The residue is recrystallized from hexane to afford 5.4 g. of 2-phenyl-3-t-butyl-5-p-toluenesulfonyloxymethyloxazolidine.

Also prepared by the above technique, but substituting the desired oxazolidine for 2-phenyl-3-t-butyl-5-p-toluenesulfonyloxymethyloxazolidine are 3-t-butyl-5-p-toluenesulfonyloxymethyloxazolidine, m.p. 69°-70° C.; and 2-methyl-3-t-butyl-5-p-toluenesulfonyloxymethyloxazolidine.

(b) A sodium hydride (57%) dispersion in mineral oil (90 mg.) is washed with pentane 3 times, and treated with 5 ml. of dry DMF. To the resulting dispersion is added 490 mg. of 4-[2-(endobicyclo[3.1.0]hex-6-yl)ethylaminocarbonyl]thiophene-2-ol dissolved in 15 ml. of DMF. After 10 minutes, 782 mg. of 2-phenyl-3-t-butyl-5-p-toluenesulfonyloxymethyloxazolidine (step a) in 5 ml. of DMF are added and the temperature of the reaction mixture raised to approximately 80° C. Stirring is continued for 2 hours. The reaction mixture is cooled, poured into 50 ml. of water, and extracted with 75 ml. of methylene chloride (three times). The combined organic layers are washed with an equal volume of water, dried over sodium sulfate, and evaporated to dryness to give the above titled oxazolidine. Purification is accomplished by column chromatography on silica gel, eluting with ethyl acetate/hexane (1:2, v/v).

EXAMPLE 8

This example is illustrative of a further method for the preparation of the compounds of the present invention having the substituent Ib.

A sodium hydride 57% dispersion in mineral oil, 2.31 g., is washed with pentane three times. Dry dimethylformamide, 500 ml., is added, followed by a solution of 12.9 g. of 2-phenyl-3-t-butyloxazolidine in 50 ml. of dry dimethylformamide. After 20 minutes, a solution of 15.75 g. 2-bromo-4-[2-(endobicyclo[3.1.0]hex-6-yl)ethylaminocarbonyl]thiophene in 50 ml. dry dimethylformamide is added slowly (15 minutes addition time). After the addition is complete the temperature of the reaction mixture is raised to 80° C. with stirring. Stirring is continued for 6 hours, the course of the reaction being monitored by TLC. When complete, the reaction is cooled, added to 150 ml. water and the aqueous solution is extracted three times with 100 ml. poritions of methylene chloride. The extracts are combined and washed three times with equal volumes of water. After drying over anhydrous magnesium sulfate, the solution is evaporated to dryness (vacuum) to give 2-phenyl-3-t-butyl-5-(3-[2-(endobicyclo[3.1.0]hex-6-yl)ethylaminocarbonyl]thien-4-yloxymethyl)oxazolidine.

EXAMPLE 9

This Example illustrates further methods of converting the compounds having the substituent Ia into the corresponding compounds having the substituent Ib. In this Example 1 mmole of 1-isopropylamino-3-(5-[2-(endobicyclo[3.1.0]hex-6-yl)ethylaminocarbonyl]thien-2-yloxy)propan-2-ol in 10 ml. of methanol is admixed with 20 ml. of 37% aqueous formaldehyde and then stirred at room temperature for one hour. The solvent is then removed by evaporation under vacuum affording a crude 3-isopropyl-5-(5-[2-(endobicyclo[3.1.0]hex-6-yl)ethylaminocarbonyl]thien-2-yloxymethyl)oxazolidine residue which is then stirred in 50 ml. of ethyl ether and filtered. Gaseous hydrogen chloride is passed over the surface of the filtrate with rapid stirring until no further precipitate is formed. The precipitate is filtered off, washed with diethyl ether and then recrystallized from a mixture of propanol and diethyl ether affording 3-isopropyl-5-(5-[2-(endobicyclo[3.1.0]hex-6-yl)ethylaminocarbonyl]thien-2-yloxymethyl)oxazolidine hydrochloride.

Similarly by following the same procedure, the products of Example 1 are respectively converted to the corresponding compounds bearing the substituent Ib and their hydrochloride salts.

Obviously many modifications and variations of the invention, described herein above and below in the Claims, can be made without departing from the essence and scope thereof.

What is claimed is:

1. A compound of the formula:

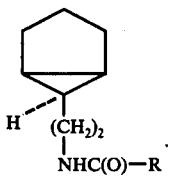

where R is

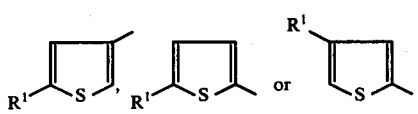

where $R^1$ is the radical $$-OCH_2\underset{\underset{OH}{|}}{C}HCH_2NHR^2$$

wherein $R^2$ is $C_1$ to $C_4$ linear or branched alkyl, and pharmaceutically acceptable salts thereof.

2. The compound of claim 1 wherein $R^2$ is isopropyl or t-butyl and pharmaceutically acceptable salts thereof.

3. The compound of claim 2 wherein $R^1$ is $$-OCH_2\underset{\underset{OH}{|}}{C}HCH_2NHR^2$$

where $R^2$ is isopropyl.

4. The compound of claim 3 wherein R is

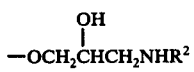

5. The compound of claim 3 wherein R is

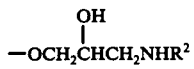

6. The compound of claim 3 wherein R is

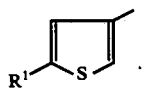

7. The compound of claim 2 wherein $R^1$ is $$-OCH_2\underset{\underset{OH}{|}}{C}HCH_2NHR^2$$

where $R^2$ is t-butyl.

8. The compound of claim 7 wherein R is

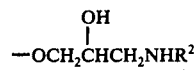

9. The compound of claim 7 wherein R is

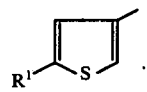

10. The compound of claim 7 wherein R is

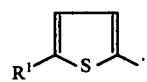

11. A pharmaceutical composition for treating cardiovascular disorders in mammals by blocking the beta-adrenergic receptor sites, consisting essentially of a pharmaceutically acceptable carrier and an amount effective to block said beta-adrenergic receptor sites of an agent selected from the group of compounds of claim 1 and mixtures thereof.

12. A pharmaceutical composition for treating cardiovascular disorders in mammals by blocking the beta-adrenergic receptor sites, consisting essentially of a pharmaceutically acceptable carrier and an amount effective to block said beta-adrenergic receptor sites of an agent selected from the group of compounds of claim 2 and mixtures thereof.

13. A pharmaceutical composition for treating hypertension disorders in mammals consisting essentially of a pharmaceutically acceptable carrier and an amount effective to treat hypertension of an agent selected from the group of compounds of claim 1 and mixtures thereof.

14. A pharmaceutical composition for treating hypertension disorders in mammals consisting essentially of a pharmaceutically acceptable carrier and an amount effective to treat hypertension of an agent selected from the group of compounds of claim 2 and mixtures thereof.

15. The compound of claim 1 wherein when said compound is a pharmaceutically acceptable salt said salt is selected from the group hydrochloride and maleate salt.

* * * * *